(12) United States Patent
Schmidt

(10) Patent No.: US 6,726,617 B1
(45) Date of Patent: Apr. 27, 2004

(54) CARTRIDGE AND APPLICATOR

(76) Inventor: Bruno Schmidt, 5836 Portsmouth Dr., Tampa, FL (US) 33615

( * ) Notice: Subject to any disclaimer, the term of this patent is extended or adjusted under 35 U.S.C. 154(b) by 0 days.

(21) Appl. No.: 10/394,967

(22) Filed: Mar. 24, 2003

Related U.S. Application Data

(63) Continuation-in-part of application No. 09/829,190, filed on Apr. 9, 2001, now Pat. No. 6,561,967.

(51) Int. Cl.[7] ............................................. A61M 36/12
(52) U.S. Cl. ....................................................... 600/7
(58) Field of Search .......................... 600/7, 8; 604/57, 604/59, 60, 61, 63, 62; 206/535; 221/198, 232, 279

(56) References Cited

U.S. PATENT DOCUMENTS

| | | | | |
|---|---|---|---|---|
| 4,451,254 A | * | 5/1984 | Dinius et al. .................. 604/62 |
| 5,522,797 A | * | 6/1996 | Grimm ........................ 604/61 |
| 6,007,474 A | * | 12/1999 | Rydell ............................ 600/7 |
| 6,102,844 A | * | 8/2000 | Ravins et al. .................. 600/8 |
| 6,213,932 B1 | * | 4/2001 | Schmidt ......................... 600/7 |
| 6,267,718 B1 | * | 7/2001 | Vitali et al. ..................... 600/7 |
| 6,358,195 B1 | * | 3/2002 | Green et al. .................... 600/7 |
| 6,561,967 B2 | * | 5/2003 | Schmidt ......................... 600/7 |
| 6,616,593 B1 | * | 9/2003 | Elliott et al. ................... 600/7 |

* cited by examiner

*Primary Examiner*—Eric F. Winakur
*Assistant Examiner*—Nikita R Veniaminov
(74) *Attorney, Agent, or Firm*—Stanley M. Miller

(57) ABSTRACT

An applicator for delivering radioactive seeds to a prostate gland or other internal organ includes a disposable inner part formed by two mating parts that collectively define a longitudinally-extending throughbore when joined together. The disposable inner part is sandwiched between two applicator half shells secured to one another by a slide member. The throughbore is discontinuous at a cartridge-receiving chamber that accommodates a multiple seed-containing cartridge, completely shielded with a sliding inspection window. The trailing end of a transition tube is held within the throughbore on a leading side of the discontinuous throughbore and the leading end of the transition tube extends into the lumen of an elongate needle. Seeds are expelled by a push rod that extends sequentially through a seed discharge chamber in the cartridge, the transition tube, and the needle. In a first alternative embodiment the disposable inner part is one piece and in a second it is formed integrally with the half shells.

21 Claims, 15 Drawing Sheets

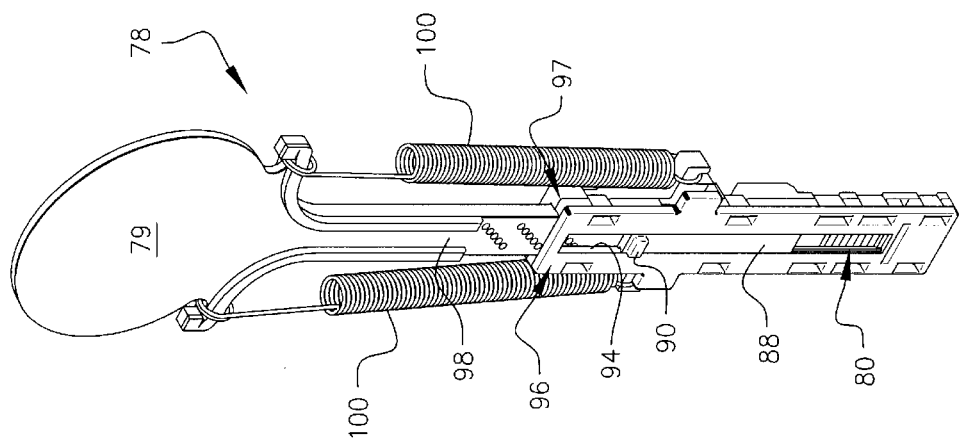
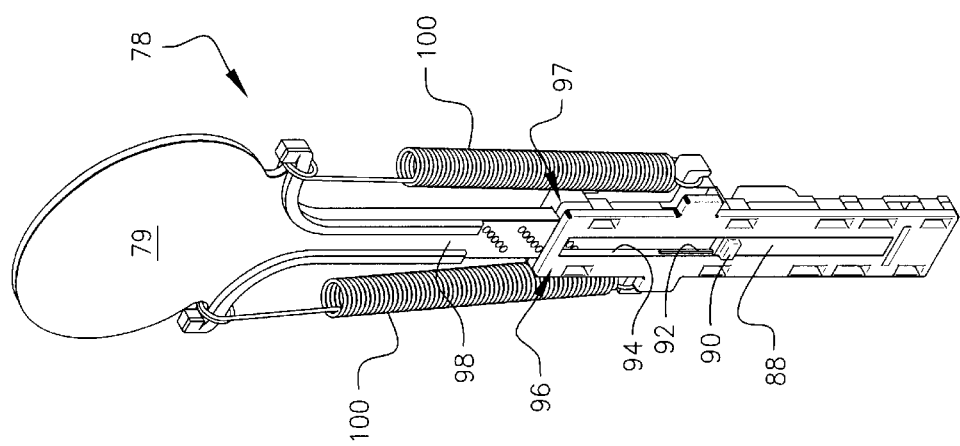

//PAGE CONTENT START

CARTRIDGE AND APPLICATOR

This application is a continuation-in-part of Ser. No. 09/829,190 filed Apr. 9, 2001 now U.S. Pat. No. 6,561,967.

BACKGROUND OF THE INVENTION

1. Field of the Invention

This invention relates, generally, to a surgical tool for implanting radioactive seeds into a prostate gland or other internal organ. More particularly, it relates to a tool having disposable parts.

2. Description of the Prior Art

Radioactive seeds are implanted into a cancerous prostate gland to kill the tumor or tumors therein. Such seeds may also be used to attack tumors in other internal organs of the body.

In use, an applicator comes into contact with a patient's blood and other body fluids. Earlier applicators were therefore designed to be disposed of after use.

For example, U.S. Pat. No. 6,213,932 to the present inventor discloses a disposable applicator having the general appearance of a hypodermic syringe. It includes a transparent plastic cartridge for holding a plurality of radioactive tumor-killing seeds. Since the entire device is disposable after use, materials used in its construction must be re-cycled to avoid wasting such materials.

Pending U.S. patent application Ser. No. 09/829,190, now U.S. Pat. No. 6,561,967 also to the present inventor, improves upon the patented tool by providing an applicator having a plurality of cartridges that are stored on the body of the applicator so that a new cartridge is easily retrieved when all of the seeds have been discharged from an old cartridge. That patent application is incorporated herein by reference. The applicator of the pending patent application includes a disposable section from the needle to where the seeds are deployed from the cartridge. This represents an improvement over the earlier device because the entire applicator need not be discarded after use.

However, the patent pending applicator is not easily disassembled for cleaning.

It would therefore be advantageous if an applicator were provided that could be easily disassembled for cleaning. It would be even more advantageous if only the parts of an applicator that directly contact body fluids would be disposable while the rest of the applicator could be taken apart and cleaned easily for re-use.

Another drawback of earlier devices is that complete shielding of the cartridges precludes visual inspection of the seeds therewithin. A physician using an applicator would prefer to visually inspect the cartridges to see how many are remaining in a cartridge at any given time. If the cartridge is shielded (offers radiation protection), it is no longer transparent.

However, in view of the prior art considered as a whole at the time the present invention was made, it was not obvious to those of ordinary skill in the pertinent art how such need could be fulfilled.

SUMMARY OF THE INVENTION

The long-standing but heretofore unfulfilled need for an improved cartridge and applicator for implanting radioactive seeds in internal organs is now met by a new, useful, and nonobvious invention. The invention includes a disposable internal part that comes into contact with a patient's blood and other body fluids. The disposable inner part is made of two elongate half parts and each half part has a longitudinally-extending groove formed therein. Moreover, each of the half parts has half of a cartridge housing formed therein as well. An elongate throughbore is formed by joining together the two half parts. Specifically, the elongate throughbore is formed by juxtaposition of the longitudinally-extending grooves.

A cartridge housing is also formed by joining together the two half parts. More particularly, the cartridge housing is formed by juxtaposition of the halves of the cartridge housing formed in said halves of said disposable inner part.

The elongate throughbore is discontinuous at the cartridge housing and has a trailing part on a trailing side of the cartridge housing and a leading part on a leading side of the cartridge housing.

The novel applicator further includes a polyimide transition tube having a trailing end captured by the leading part of the elongate throughbore. The transition tube has a leading end that extends from the elongate throughbore in leading relation thereto and the transition tube leading end is adapted to be positioned within a lumen of an elongate needle that has a sharp distal end for penetrating tissue.

The novel applicator outer shell is formed by two half shells. Each of the two outer half shells has a longitudinally-extending half-channel formed therein. An elongate channel is formed by joining together the two half shells in juxtaposition with one another.

A cartridge housing-receiving recess is formed in each of the half shells. Each half channel is discontinuous at the cartridge housing-receiving recess. The disposable inner part, including the cartridge housing, is disposed in sandwiched relation between the half shells when the half shells are in juxtaposition with one another.

A longitudinally-extending groove is formed in an external side wall of each of the half shells. A slide member has a generally "U"-shaped configuration that includes a pair of upstanding side walls projecting from a base wall in parallel relation to one another. A longitudinally-extending tongue is formed in each side wall of the pair of side walls. The longitudinally-extending tongues protrude toward one another so that the longitudinally-extending tongues respectively slideably engage the longitudinally-extending grooves formed in the exterior side walls of the applicator half shells.

The applicator half shells are held in juxtaposition to one another by the slide member to form the applicator shell. Removal of the slide member from the applicator half shells enables cleaning of the slide member and the applicator half shells.

An elongate rod is secured to and projects from the slide member in leading relation thereto. A "U"-shaped support member is secured to a leading end of the elongate rod.

A transversely disposed handle is secured to a trailing end of a preselected applicator half shell. The transversely disposed handle is centered with respect to the applicator shell when the applicator half shells are joined together.

The novel seed cartridge for holding radioactive seeds includes a seed housing adapted to hold a plurality of radioactive seeds. The seed housing includes a shielded front plate and a shielded door is formed in the front plate. The shielded door is adapted to be opened and closed so that seeds within the seed housing may be viewed when the shielded door is open and so that the seeds within the seed housing may not be viewed when the shielded door is closed. The shielded door and shielded front plate protect an ambient environment from radiation when the door is closed.

More particularly, a vertically extending opening is formed in the front plate and a vertically extending tongue is formed in opposite vertically extending edges of the vertically extending opening. A vertically extending groove is formed in each vertically extending edge of the shielded door and a door handle is secured to the shielded door so that a user may slide the door in the opening in a first direction to view seeds disposed in the housing and so that a user may slide the door in the opening in a second direction to close the door.

In a second embodiment of the invention, the disposable internal parts are integrally formed with one another.

In a third embodiment of the invention, the disposable internal parts are integrally formed with the two applicator half shells.

An important object of this invention is to provide an applicator having disposable internal parts that directly contact a patient's blood and other body fluids.

Another important object is to provide an applicator that is easily disassembled so that the internal parts requiring disposal are easily separated from the rest of the applicator for such disposal.

Still another object is to provide an applicator where the parts thereof that do not require disposal are easily assembled and disassembled and easily cleaned for re-use.

Yet another object is to provide a cartridge having a sliding door so that a physician may slide the door open to view the seeds, and to slide the door closed to restore the shielding function of the door, thereby preventing radiation leakage in all directions.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 9 is a perspective view of a cartridge with the viewing door closed;

FIG. 10 is a perspective view of the cartridge of FIG. 9 with the seed viewing door open;

DETAILED DESCRIPTION OF THE PREFERRED EMBODIMENT

Figure 1:
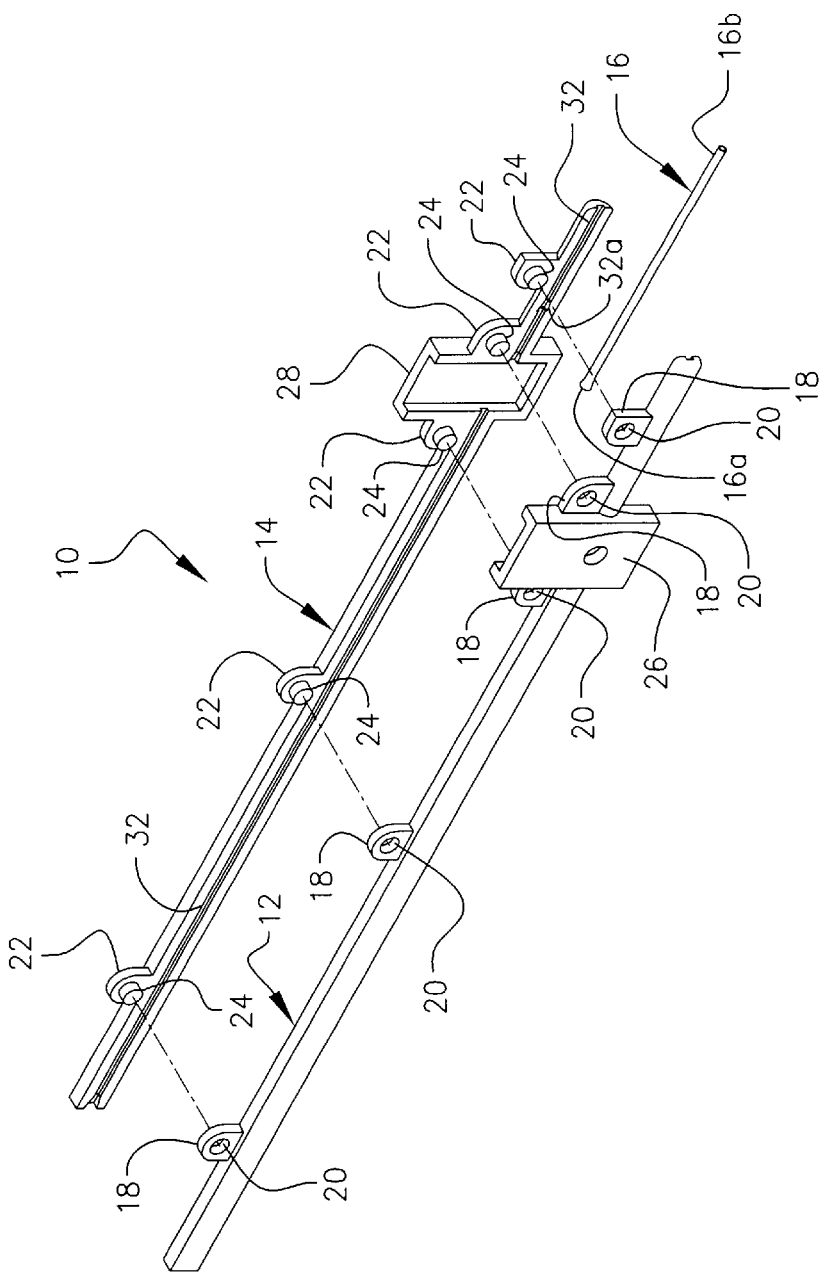
FIG. 1 is an exploded perspective view of the disposable internal parts of the novel applicator.

Referring to FIG. 1, it will there be seen that the reference numeral 10 denotes an illustrative embodiment of the present invention as a whole.

All of the parts denoted by the reference numeral 10 are the internal, disposable parts of the novel applicator and are hereinafter referred to as the "guts." The guts are the parts of the applicator that come into contact with the blood and other body fluids of the patient.

Guts 10 include parts 12, 14, and 16. Part 12 has an elongate straight base and a plurality of ears, collectively denoted 18 integrally formed therewith in longitudinally spaced apart relation to one another. Each ear 18 is centrally apertured as at 20.

Part 14 has an elongate straight base and a plurality of ears, collectively denoted 22 integrally formed therewith in longitudinally spaced apart relation to one another. Each ear 22 has a centrally mounted protrusion 24 that interlocks with an associated central aperture 20 to thereby join parts 12 and 14 to one another. The interconnection between parts 12 and 14 may rely on a press fit or an adhesive may be used to supplement the interconnection.

Half cartridge housing 26 is formed integrally with part 12 and half cartridge housing 28 is formed integrally with part 14. As best understood in connection with FIG. 2, said half cartridge housings 26, 28 together form cartridge housing 30 when parts 12 and 14 are joined to one another.

Returning to FIG. 1, it will there be seen that groove 32 is formed along the entire extent of part 14. A mating groove, not shown, is formed in part 12 so that an elongate bore that extends from the trailing end of the assembled parts 12 and 14 to the leading end thereof is formed when said two parts are joined together as depicted in FIG. 2.

As best understood in connection with FIG. 1, transition tube 16, preferably formed of polyimide, has a slightly enlarged trailing end 16a that is received with the elongate bore formed when groove 32 formed in part 14 and its unillustrated counterpart formed in part 12 are in juxtaposition with another. Groove 32 and its unillustrated counterpart are slightly enlarged as at 32a to accommodate the slightly enlarged trailing end 16a of polyimide transition tube 16 so that when parts 12 and 14 are joined to one another in sandwiching relation to transition tube 16, said enlarged trailing end 16a is captured within said enlargement 32a to ensure that polyimide transition tube 16 does not slide out of said throughbore.

Figure 2:
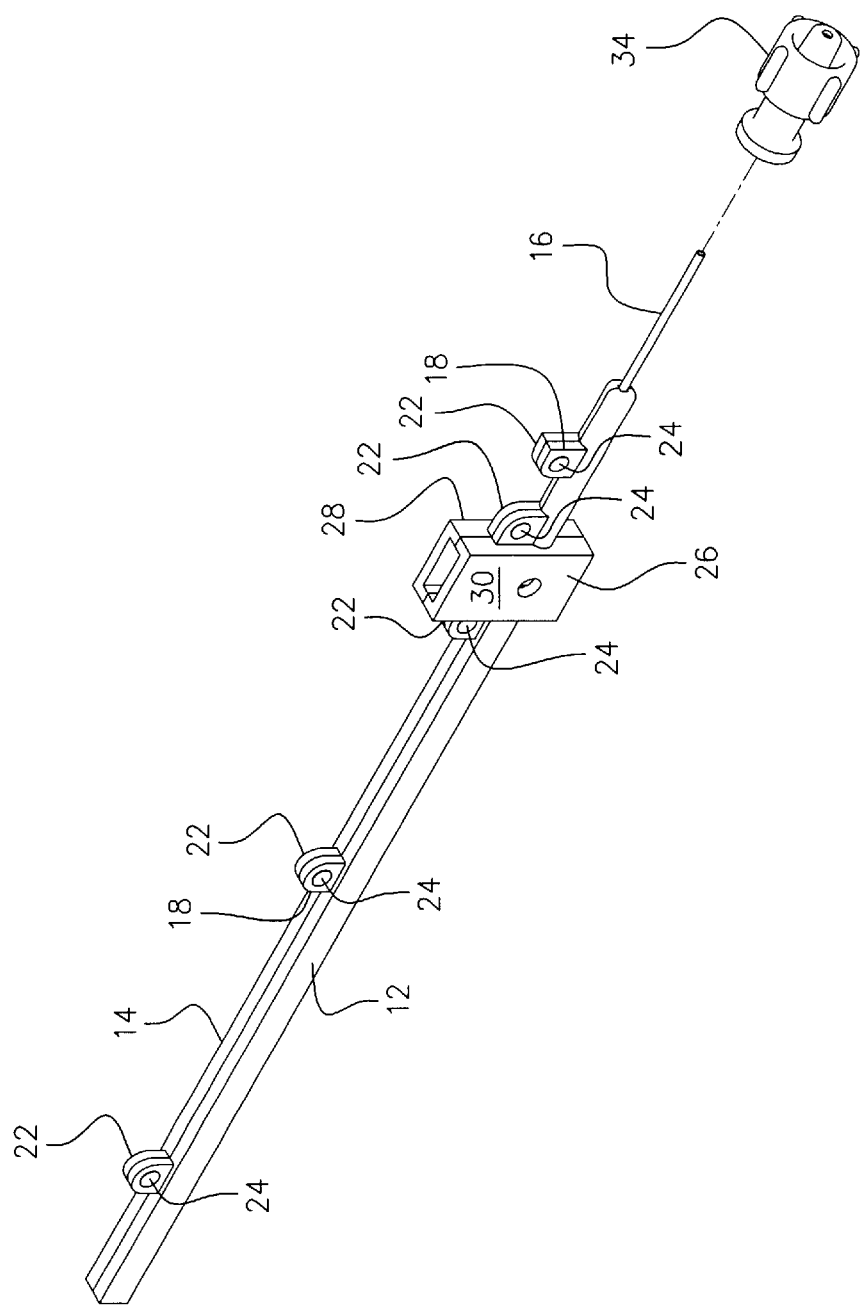
FIG. 2 is a perspective view of the assembled internal parts and further depicting how a luer lock is attached thereto.

Polyimide transition tube 16 is depicted in its captured relation to parts 12 and 14 in FIG. 2.

Returning again to FIG. 1, it should be observed that groove 32 formed in part 14 and its unillustrated counterpart formed in part 12 is discontinuous at cartridge housing 30. When a cartridge is positioned within cartridge housing 30, a radioactive seed is positioned in alignment with the throughbore formed by groove 32 and its unillustrated counterpart. An elongate plunger, not depicted in FIGS. 1 and 2, is introduced into the trailing end of the throughbore defined by disposable guts 10 and the leading end of said plunger bears against the trailing end of the seed in cartridge housing 30 and pushes it towards the leading end of the throughbore so that said seed enters into transition tube 16. The leading end of polyimide transition tube 16, denoted 16b in FIG. 1, is received within the lumen of an elongate needle, not illustrated in FIGS. 1 and 2, that is in turn inserted into the prostate or other organ into which the radioactive seeds are to be implanted.

Figure 3:
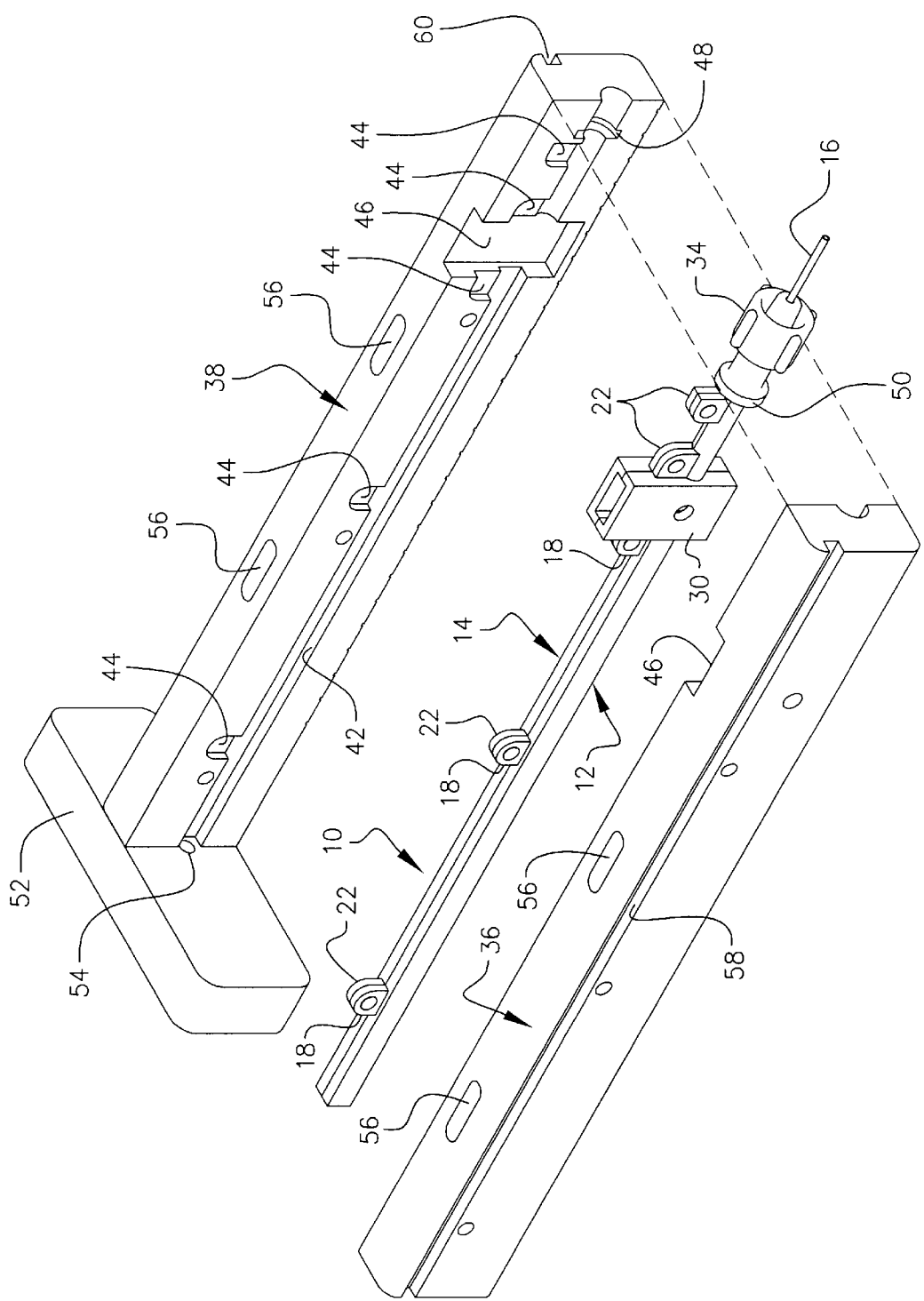
FIG. 3 is an exploded perspective view depicting the applicator shell that houses the disposable internal parts.

As indicated in FIGS. 2 and 3, a luer lock base 34 or equivalent device is mounted to transition tube 16. Luer lock base 34 is adapted to provide a mounting means for any luer lock or screw-in type needle.

Figure 4:
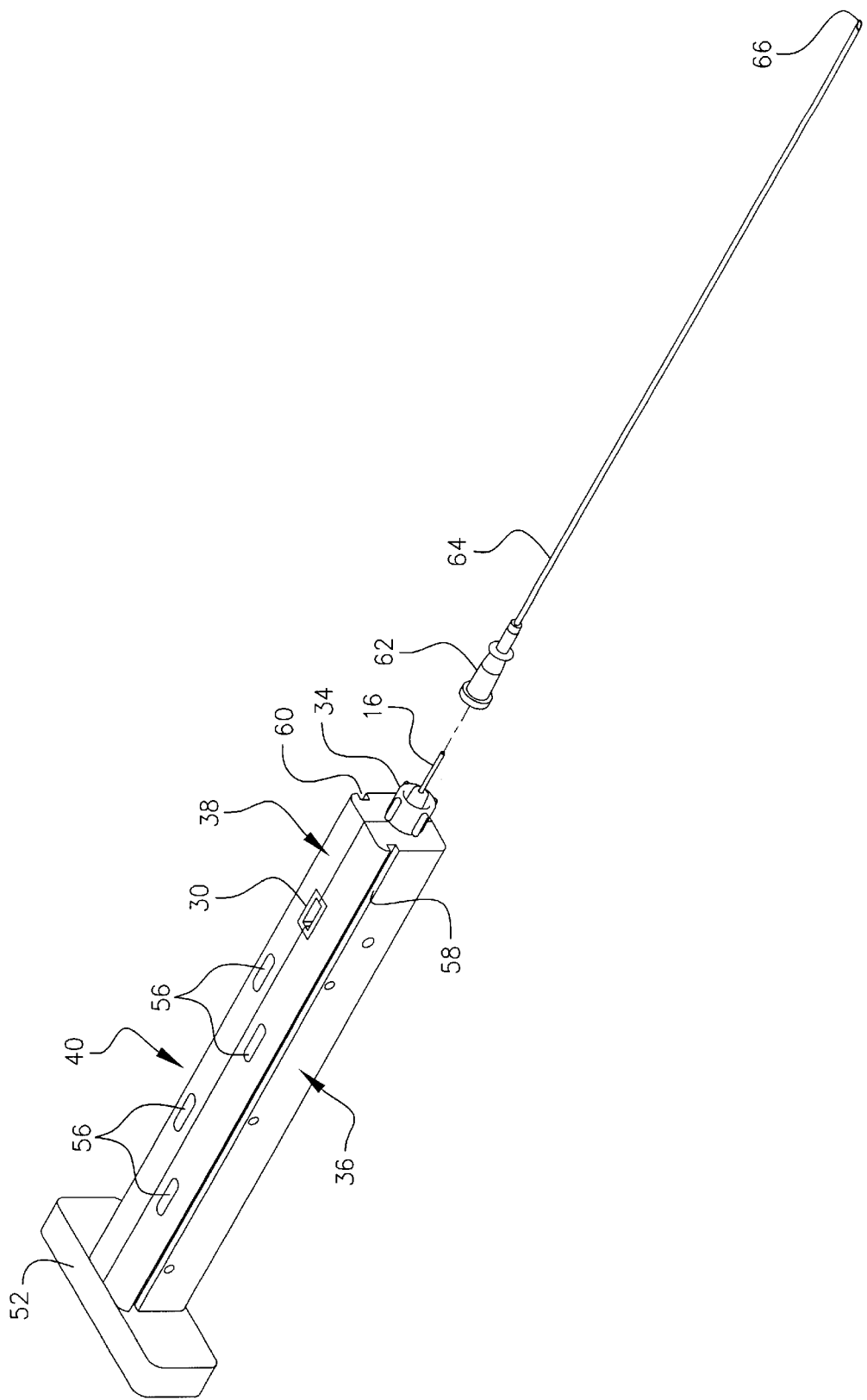
FIG. 4 is a perspective view depicting the applicator shell in its assembled configuration and further depicts how an elongate needle is attached to the luer lock fitting.

Applicator shell 40, depicted in FIG. 4, is formed of two parts 36 and 38 as best understood in connection with FIG. 3. Half channel 42 formed in part 38 has an unillustrated counterpart in part 36 to accommodate guts 10 when parts 36 and 38 are assembled together. Recesses 44 accommodate ears 22 and unillustrated recesses formed in part 36 accommodate ears 18. Recesses 46 accommodate cartridge housing 30 and annular groove 48, only half of which is depicted, accommodates flange 50 formed in the trailing end of luer lock base 34. Luer lock base 34 abuts the leading end of applicator shell 40 when it is fully assembled as depicted in FIG. 4.

Transversely disposed handle 52 is formed integrally with applicator half shell 38 at the trailing end thereof.

Longitudinally-extending bore 54 is formed in said handle 52 to admit a pushrod into the throughbore formed when the two parts of guts 10 are assembled as mentioned above.

Openings 56 formed in applicator half shell parts 36 and 38 are adapted to accommodate cartridges that are not in use when a seed-implanting procedure is performed, as more fully set forth in the incorporated pending patent application.

It should also be observed in FIGS. 3 and 4 that elongate slots 58 and 60 are formed in applicator half shell parts 36 and 38, respectively. Said elongate slots extend the entire extent of said half shell parts and are formed on respective exterior surfaces thereof.

FIG. 4 further depicts luer lock main body 62 that engages luer lock base 34 in a well-known way. Elongate needle 64 is engaged at its trailing end by said luer lock main body 62. Radioactive seeds, not depicted in FIG. 4, are driven from the sharp distal end 66 of elongate needle by a push rod, not depicted in said Figure, when the inventive structure is in use. Sharp distal end 66 of needle 64 is adapted to penetrate tissue.

Figure 5:
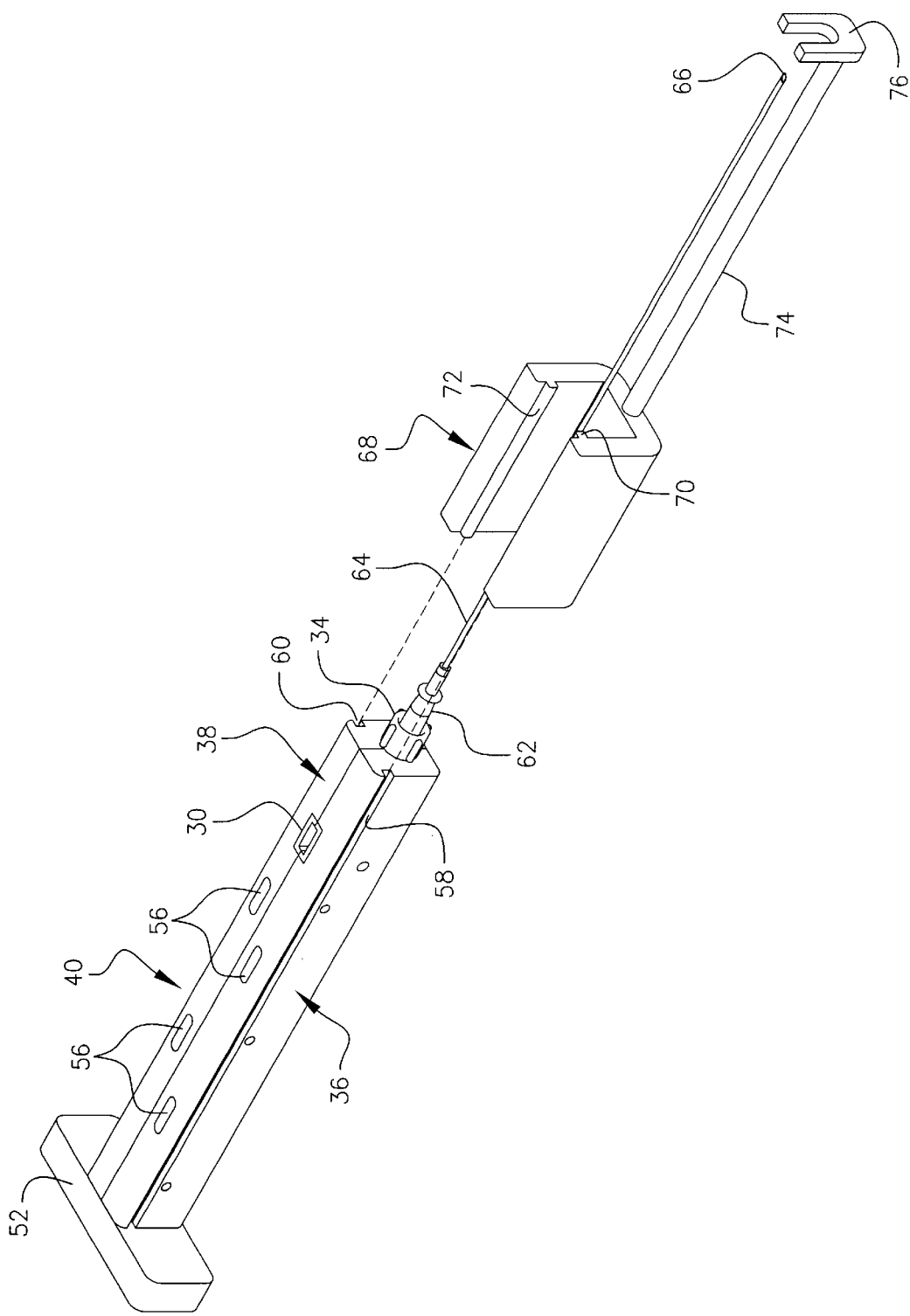
FIG. 5 is a perspective view depicting a slide member that holds together the two parts of the applicator shell and that further provides a needle support.

FIG. 5 depicts slide member 68 having an elongate "U" or channel-shaped structure including a pair of upstanding side walls projecting from a base wall in parallel relation to one another. A longitudinally-extending tongue 70, 72 is formed in each side wall of said pair of side walls. Said longitudinally-extending tongues protrude toward one another so that they respectively slideably engage longitudinally-extending grooves 58 and 60, respectively, formed in said exterior side walls of said applicator half shells as indicated by the dotted assembly lines. Slide member 68 is used to hold together the two half parts 36 and 38 of applicator shell 40.

Figure 6:
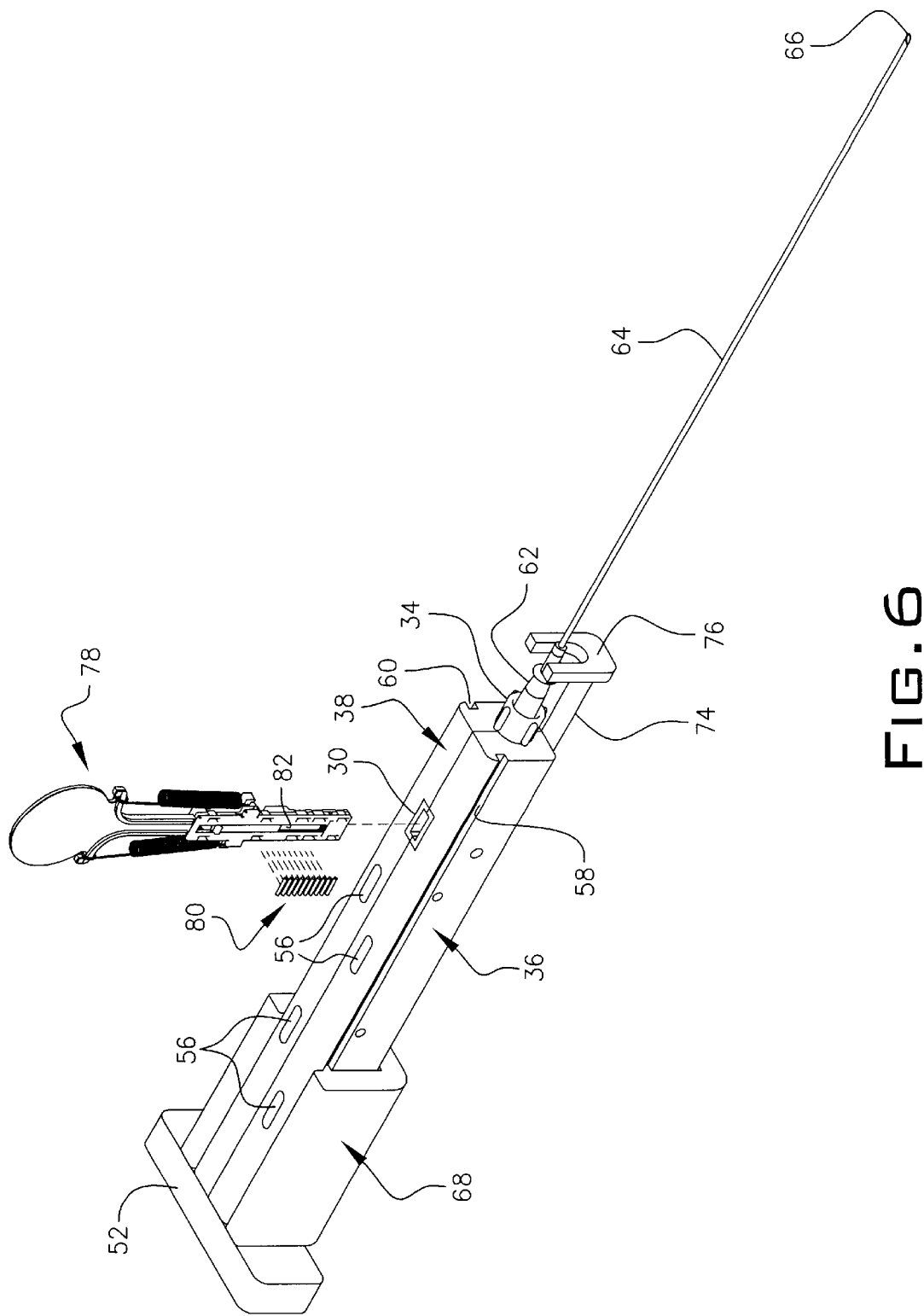
FIG. 6 is a perspective view depicting the slide member in its assembled configuration with the applicator shell and further depicting a cartridge and seeds in exploded view.

As depicted in FIG. 6, slide member 68 abuts handle 52 when the novel applicator is in use. Applicator shell 40 is centered with respect to handle 52 when applicator shell half parts 36, 38 are secured to one another by slide member 68.

As best depicted in FIG. 5, elongate rod 74 is secured to and projects from slide member 68 in leading relation thereto. "U"-shaped support member 76 is secured to the leading end of elongate rod 74.

As perhaps best understood in connection with FIG. 6, "U"-shaped support member 76 cooperates with handle 52 to provide a stable support for applicator shell 40 when it is in use. As explained in the incorporated pending patent application, said seeds may be implanted by holding applicator shell 40 against movement and advancing the push rod, or by holding the push rod against movement and retracting applicator shell 40. Either relative movement expels the seeds through distal end 66 into an internal organ. In the preferred technique, handle 52, slide member 68, and "U"-shaped support member 76 collectively anchor against the needle grid and serve as a purchase to retract needle 64 as the seeds are deployed.

FIG. 6 further depicts seed cartridge 78 that holds a plurality of seeds 80. The leading end of seed cartridge 78 is inserted into cartridge housing 30 as indicated by the dotted lines when the novel assembly is in use. The structure of seed cartridge 78 is fully disclosed in the incorporated pending patent application.

Seed cartridge 78 of this invention differs, however, in that it includes an opaque, shielded, slideably-mounted window that the physician may momentarily slide open to view seeds 80 and slide closed to provide shielding in all directions. The window rides on a tongue and groove track, disclosed hereinafter.

Figure 7:
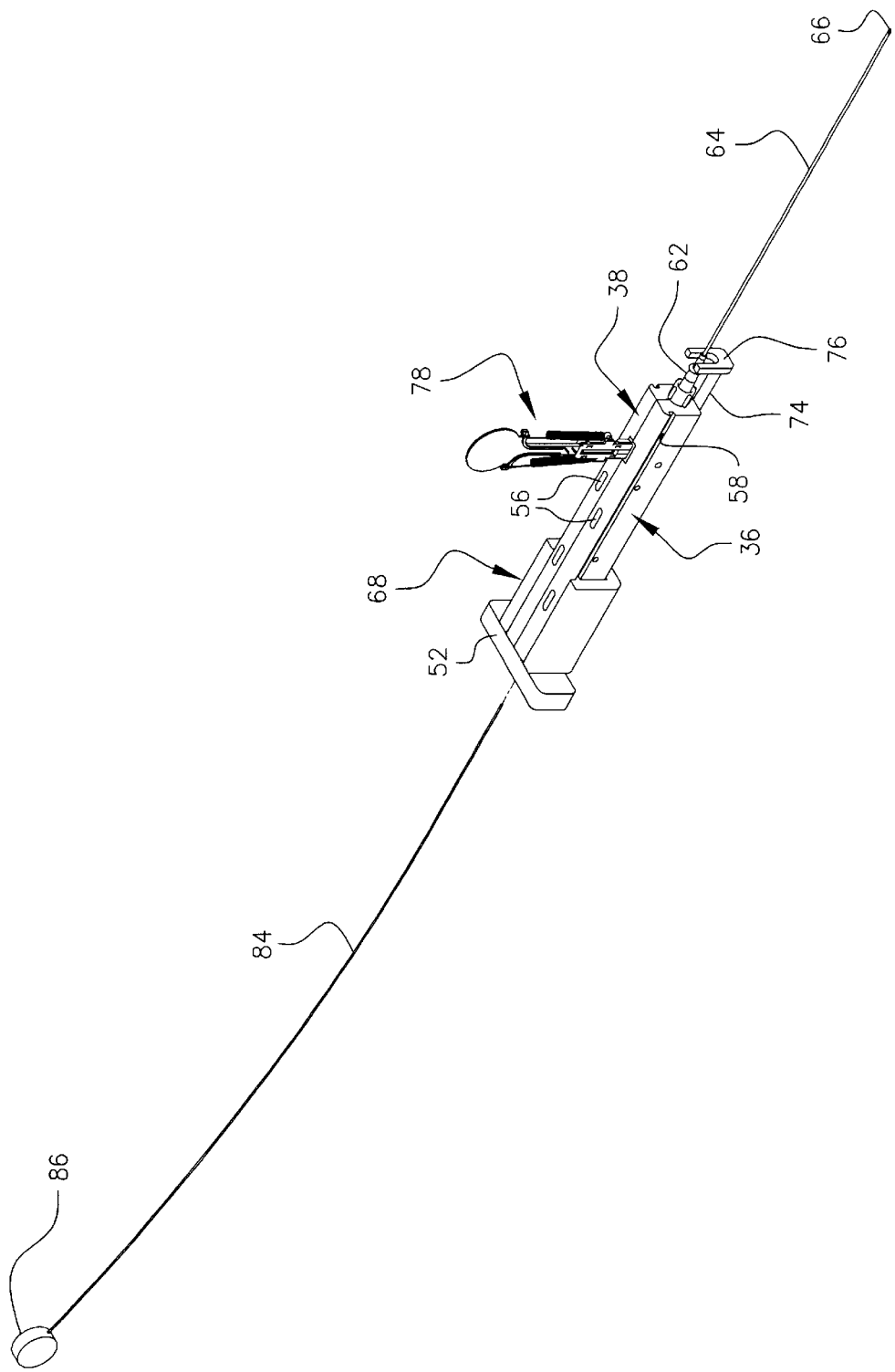
FIG. 7 is a perspective view like FIG. 6 but further adds an elongate plunger rod that pushed radioactive seeds from a seed discharge chamber in the applicator through the elongate needle and into an internal organ.

FIG. 7 depicts push rod 84 having handle 86 at its trailing end. The dotted line at the leading end of push rod 84 indicates how said push rod is introduced into the throughbore defined by the disposable guts of the applicator.

Figure 8:
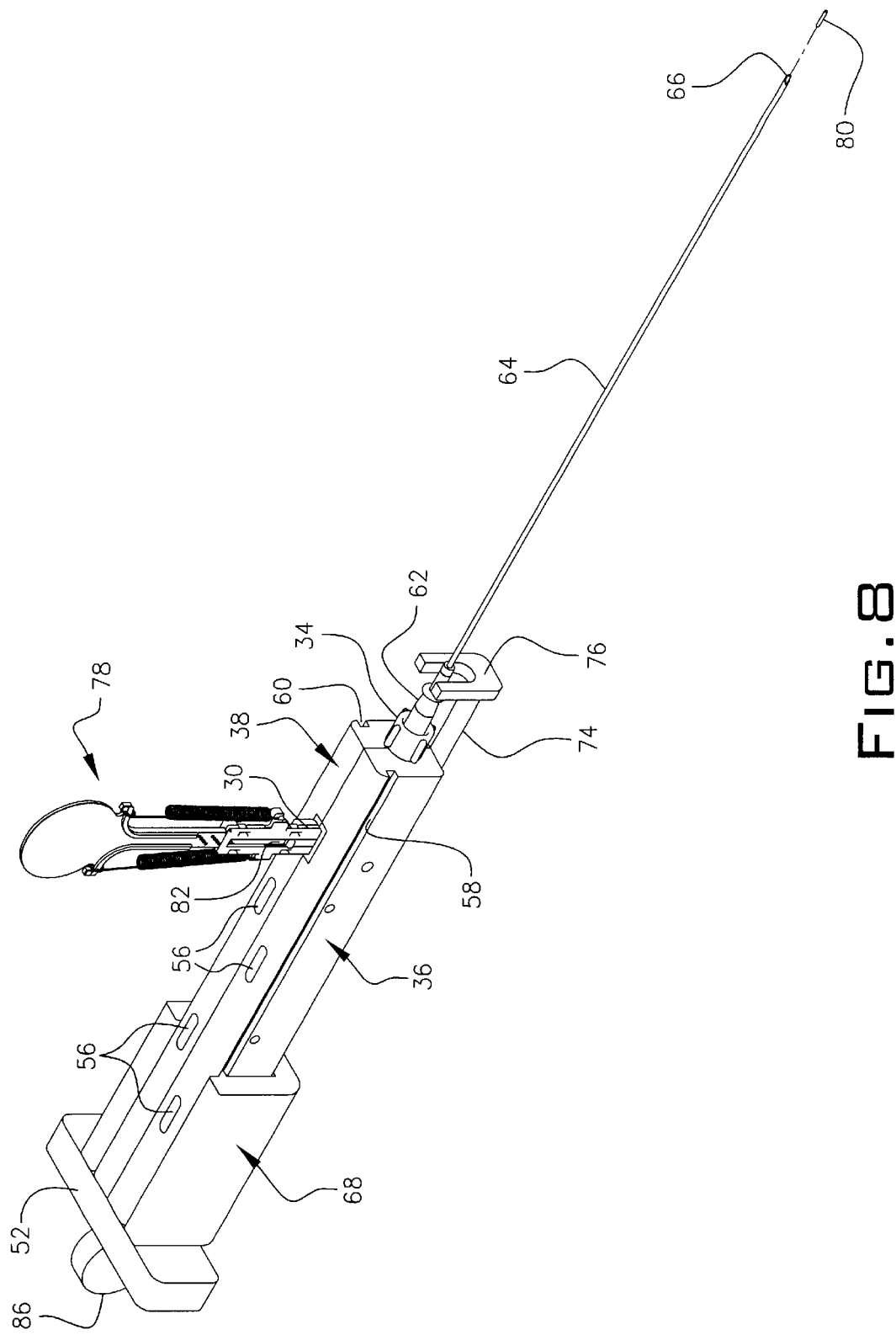
FIG. 8 is a perspective view depicting the plunger of FIG. 7 when fully inserted into the applicator so that a seed is discharged from the distal end of the elongate needle.

FIG. 8 depicts push rod 84 when fully inserted into said throughbore. A seed 80 is depicted being expelled into an internal organ from the leading end 66 of needle 64.

FIG. 9 depicts seed cartridge 78 having cartridge handle 79 and a slideably mounted shielded door 88 of elongate vertical construction. Door handle 90 is formed integrally with door 88. A vertically extending groove is formed in shielded door 88 in each of its opposite vertically extending edges. Each groove slideably engages a vertically extending tongue 92 formed on each side of vertically extending opening 94 which is formed in front plate 96 that forms a part of seed housing 97 of seed cartridge 78. Neck 98 is urged into said seed housing 97 by biasing means 100, 100 that extend in tension between said seed housing 97 and said neck 98.

The tongue and groove connection may be reversed, with a tongue formed in each vertically extending opposite edge of door 88 and a groove formed in each vertically extending opposite edge of opening 94.

FIG. 10 depicts shielded door 88 in its open configuration. Seeds 80 can be seen and counted by the physician when said door is open. Door 88 is kept closed at all other times and its shielding along with the shielding of front cover 96, rear housing 97, and handle 79 prevent radiation from escaping into the ambient environment.

Applicator shell 40 and slide member 68 are easily cleaned and re-used. The absence of a need to re-cycle or discard said parts results in a significant saving of materials.

However, in an additional embodiment, applicator shell 40 could be formed integrally with disposable guts 10 so that only slide member 68 would be retained and cleaned.

Figure 11:
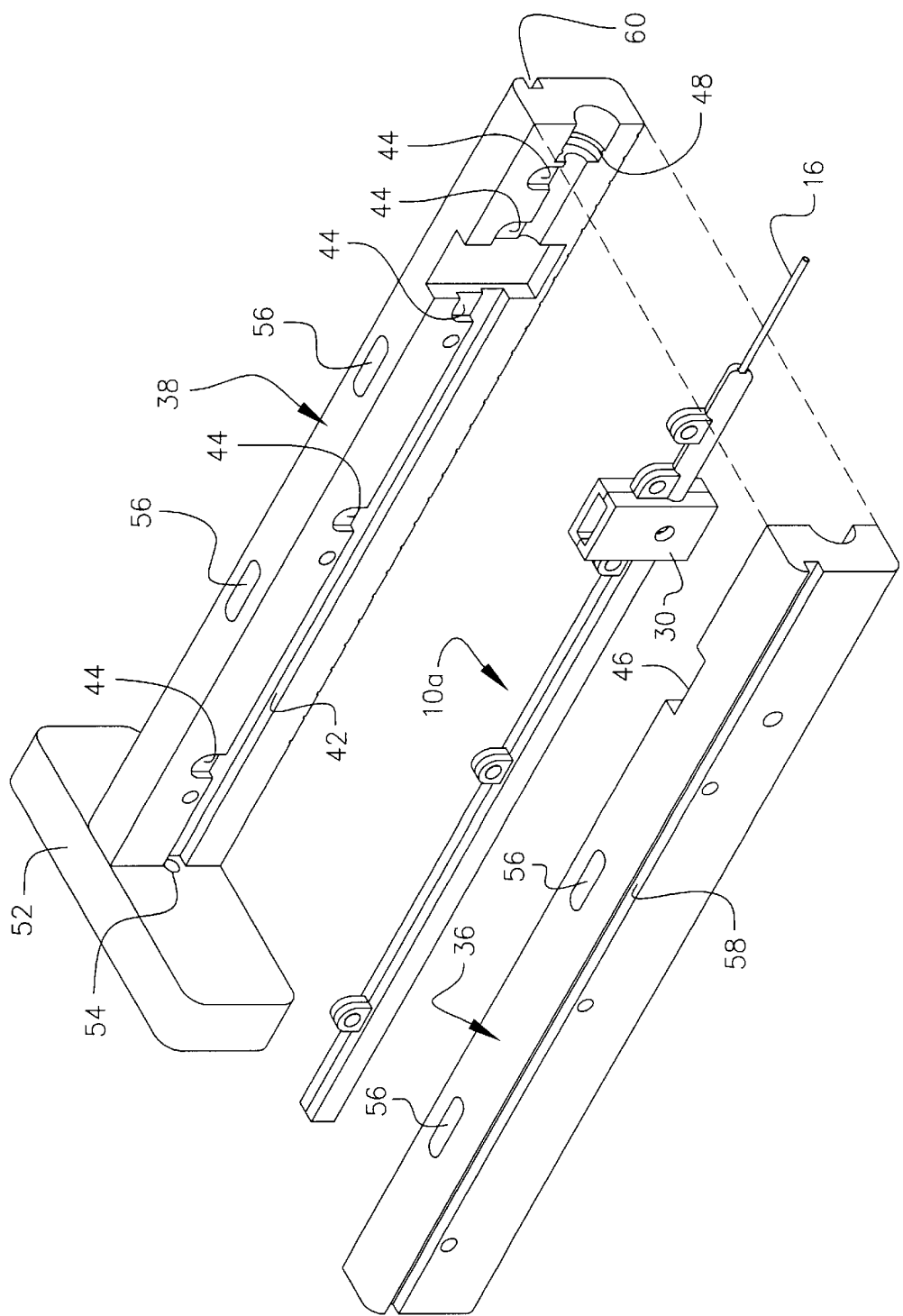
FIG. 11 is an exploded perspective view of an embodiment where the disposable internal parts of the novel applicator formed of three parts in FIG. 1 are combined into one part.
Figure 12:
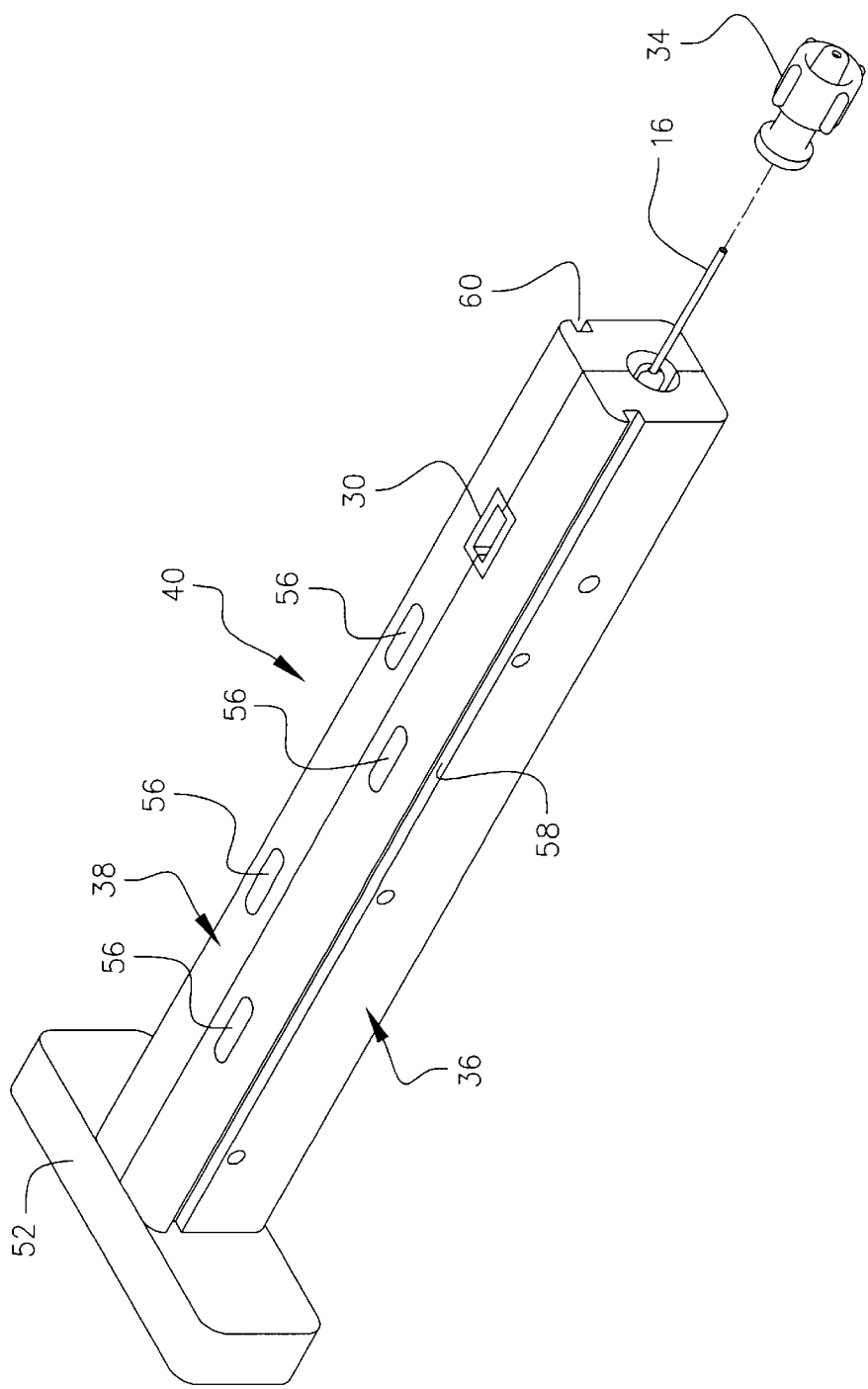
FIG. 12 is a perspective view depicting an assembly that is alternative to the assembly of FIG. 3 where the applicator shell that houses the disposable internal parts is assembled prior to the luer lock base being inserted thereon.
Figure 13:
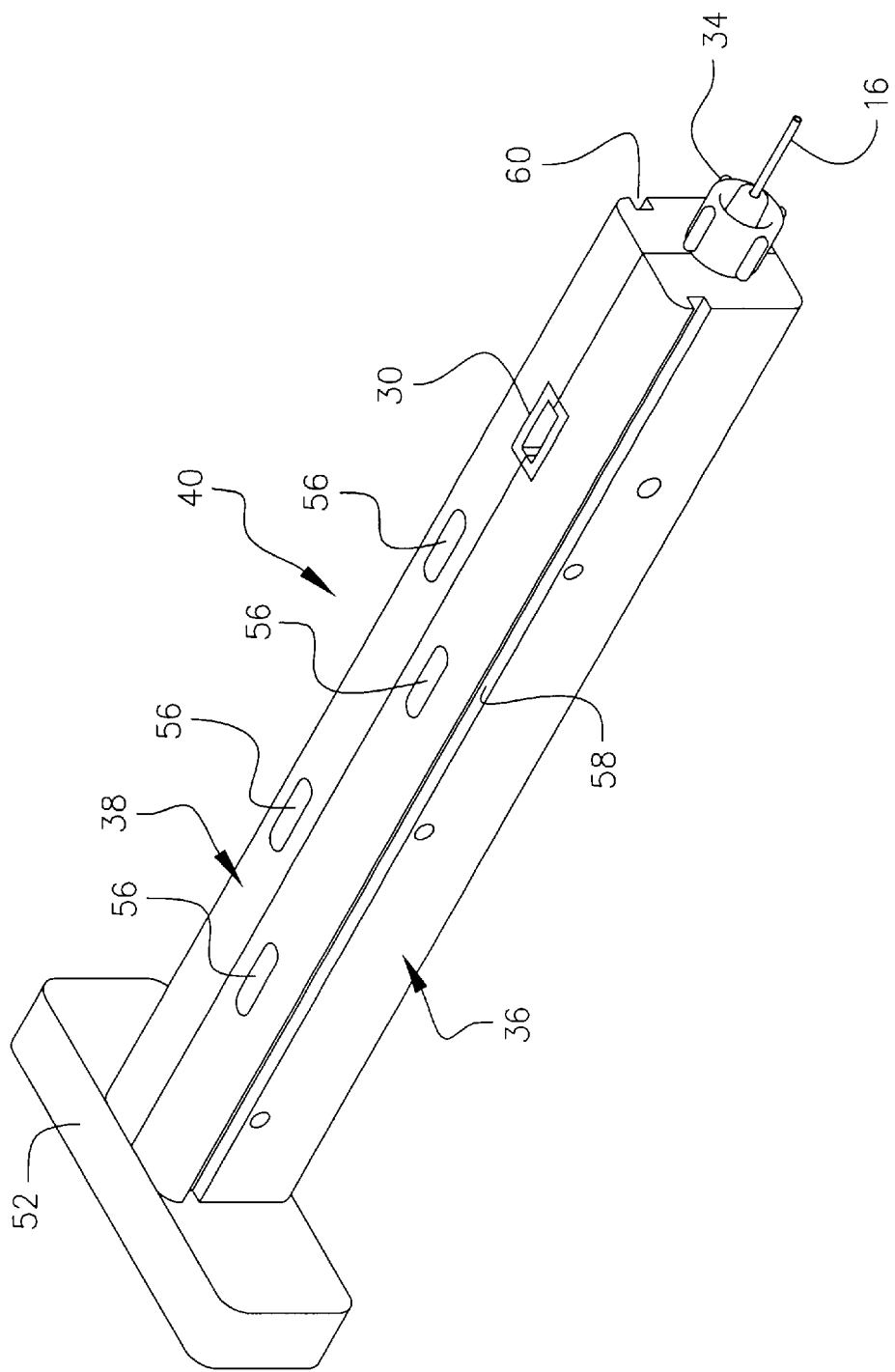
FIG. 13 is a perspective view depicting the assembly of the parts depicted in FIGS. 11 and 12, which assembly is the same as depicted in the upper left of FIG. 4.

An alternative assembly depicted in FIGS. 11–13 is best understood by referring again to FIG. 1 where internal disposable parts or guts 12, 14, and 16 are depicted in unassembled configuration. In the assembly of FIG. 11, disposable internal parts 12, 14, and 16 are pre-assembled, i.e., polyimide transition tube 16 is sandwiched between parts 12 and 14. The integrally formed guts are denoted 10a in FIG. 11. Applicator shell halves 36 and 38 are then brought into sandwiching relation to said guts as depicted in FIG. 12, prior to the addition of luer lock base 34 (FIG. 12) thereto. This differs from the assembly depicted in FIGS. 3 and 4 where luer lock base 34 is mounted to polyimide transition tube 16 (FIG. 3) prior to the step of bringing together applicator half shells 36, 38. However, the next step of the alternative assembly procedure, where luer lock base 34 is mounted onto polyimide transition tube 16, as depicted in FIG. 13, results in the same structure as depicted in the upper left of FIG. 4.

Figure 14:
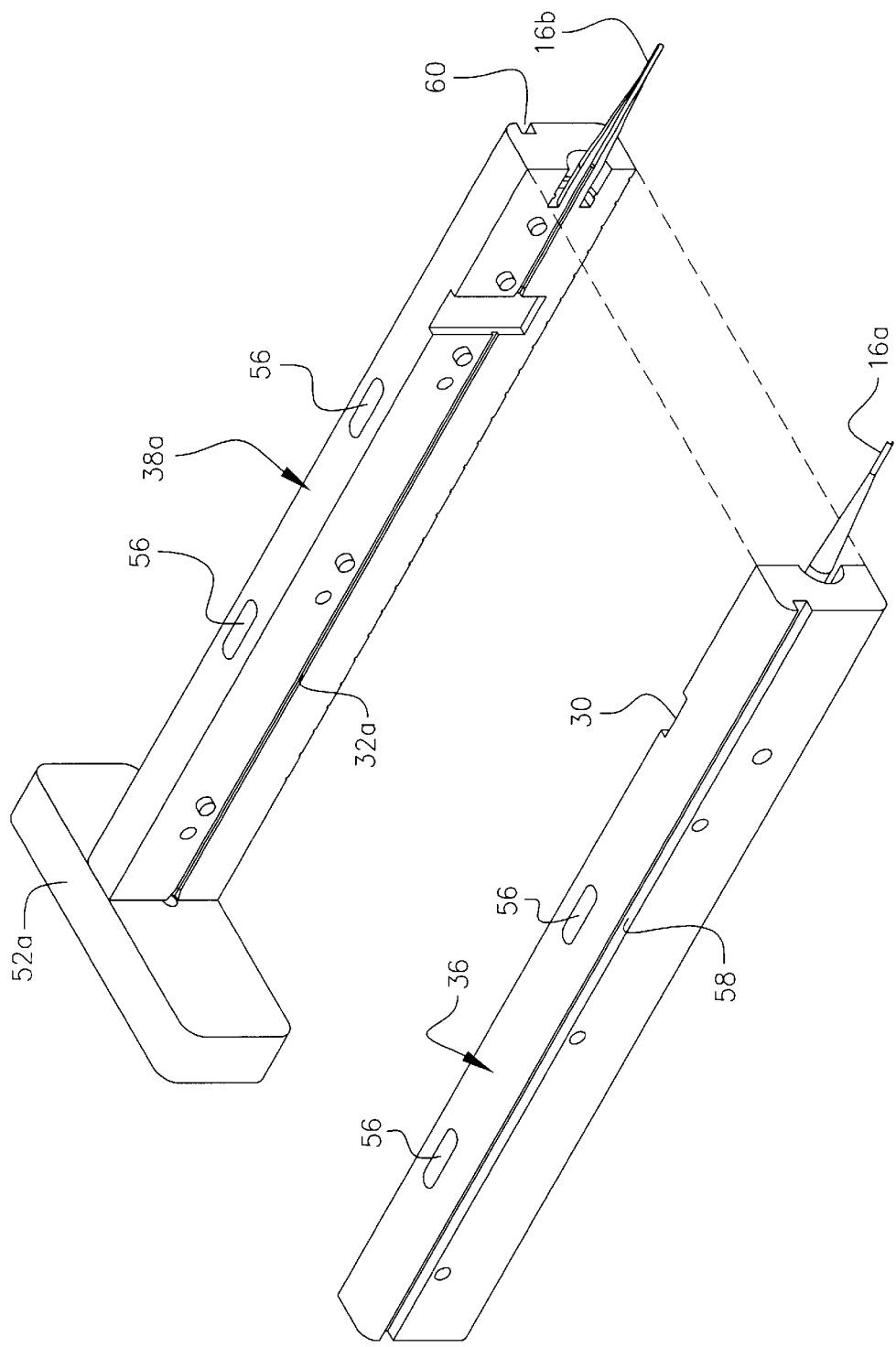
FIG. 14 is an exploded perspective view of an alternative embodiment of the applicator half shells where the internal disposable parts are eliminated as separate parts and become an integral part of the applicator half shells.
Figure 15:
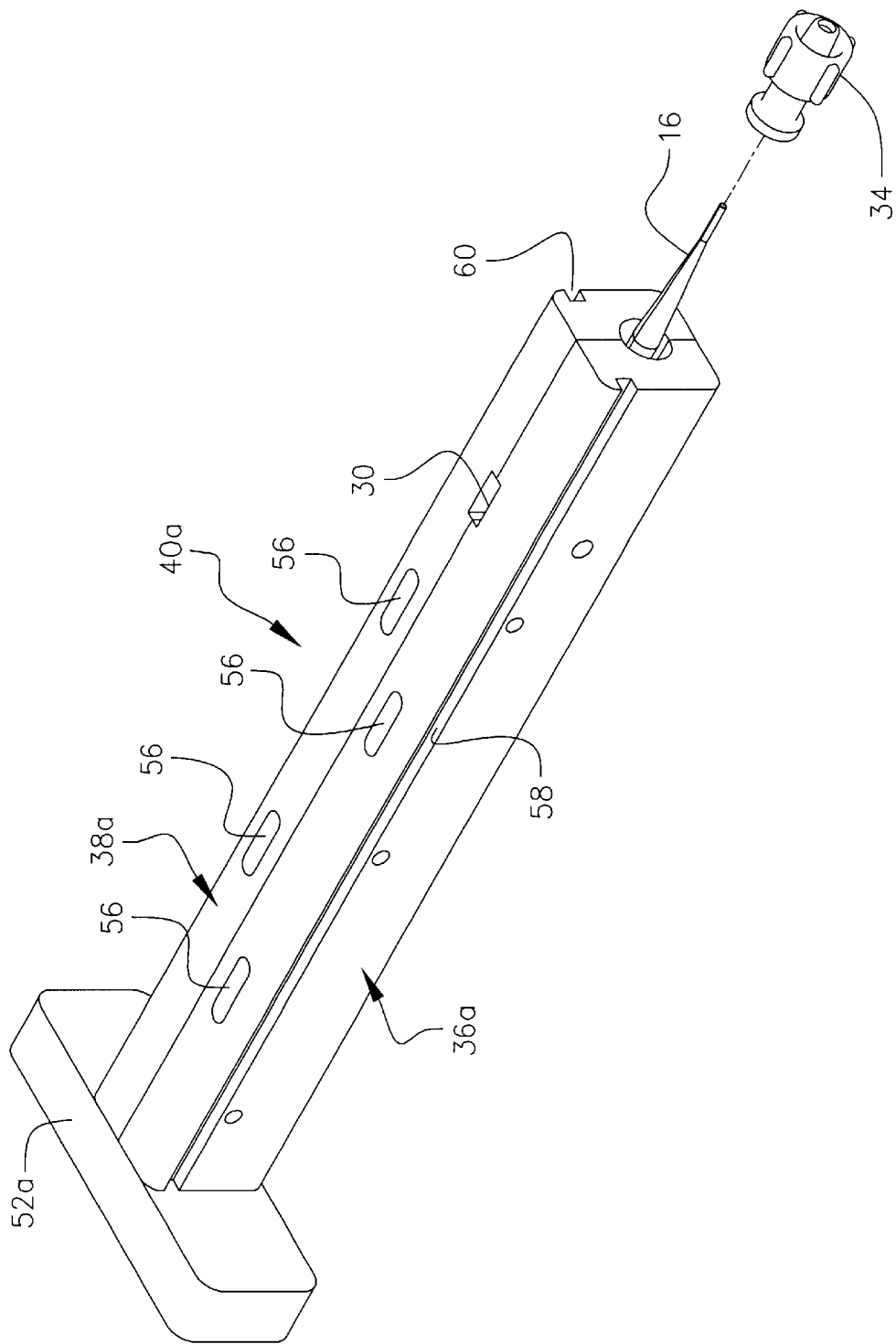
FIG. 15 is a perspective view depicting an alternative assembly where the applicator half shells of FIG. 14 are joined to one another prior to the mounting of the luer lock base thereto.
Figure 16:
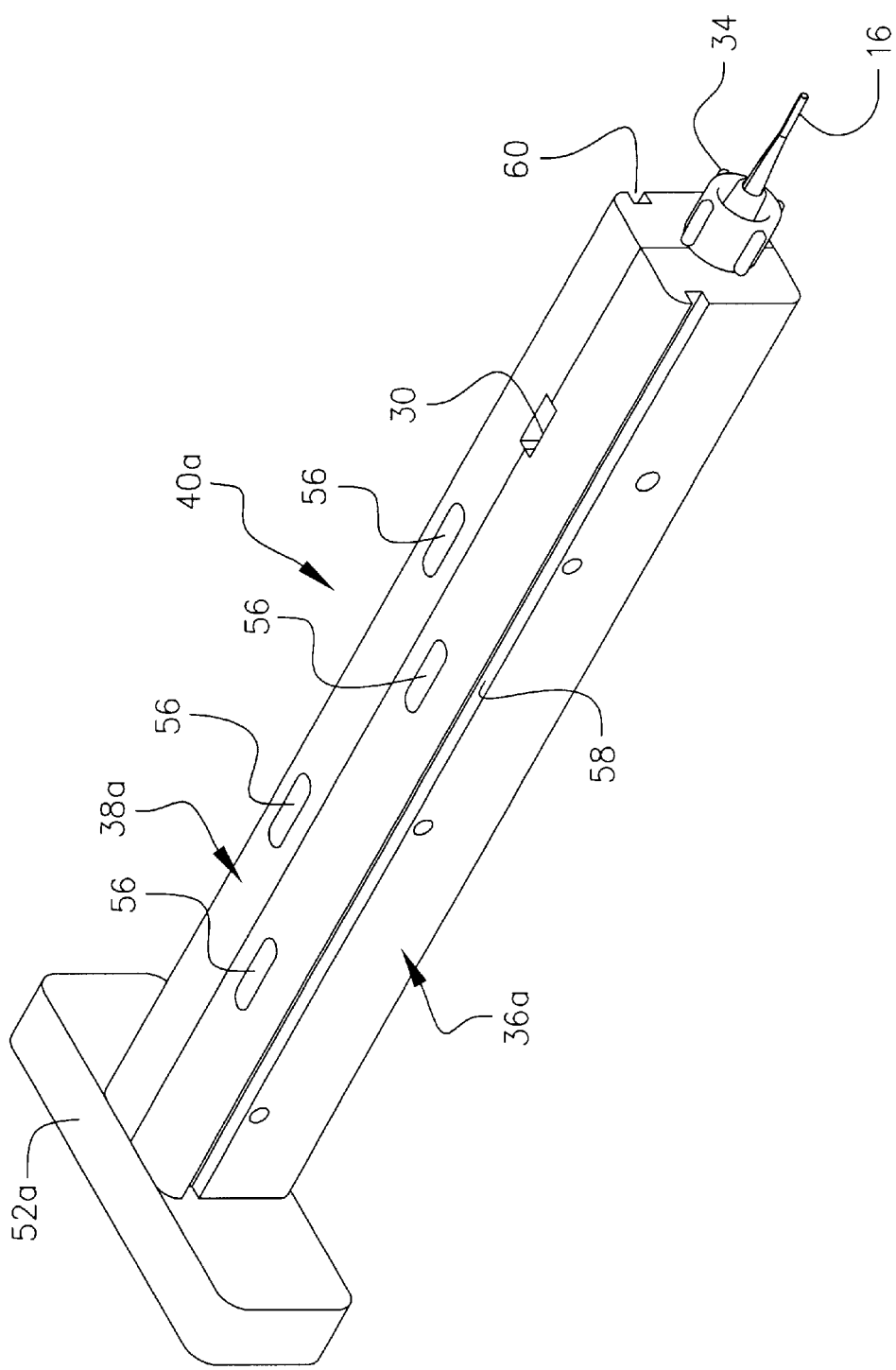
FIG. 16 is a perspective view depicting the assembly of the parts depicted in FIG. 15, which results in the same assembly as depicted in the upper left half of FIG. 4 and in FIG. 13.

Another improvement is depicted in FIGS. 14–16. As perhaps best understood by comparing FIGS. 11 and 14, disposable inner parts 12, 14, and 16 are merged into, i.e., integrally formed with applicator half shells 36a and 38a. Note that polyimide transition tube 16 is now formed and replaced with integral molding of half shell 36a and when part 16a of applicator half shell 36a is brought into juxtaposition with part 16b of applicator half shell 38a. Similarly, groove 32 is now formed when half groove 32a formed in applicator half shell 38a is brought into juxtaposition with an unillustrated mating half groove formed in applicator half shell 36a.

In this way, all three separate disposable inner parts 12, 14, and 16, are eliminated. As in the embodiment of FIGS. 11–13, applicator half shells 36a, 38a are assembled prior to the mounting of luer lock base 34 onto polyimide transition tube 16a and the final structure is depicted in FIG. 16. Groove 32a is formed in half shell 36a and 38a and is not defined by the disposable internal parts as in the earlier embodiments. Groove 32a and its unillustrated counterpart formed in half shell 36a are thus in fluid communication with the lumen formed by integrally formed transition tube 16.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. An applicator for depositing radioactive seeds into an internal organ for therapeutic purposes, comprising:
   a disposable internal part that comes into contact with a patient's blood and other body fluids;
   said disposable inner part made of two elongate half parts;
   each of said half parts having a longitudinally-extending groove formed therein;
   each of said half parts having half of a cartridge housing formed therein;
   an elongate throughbore formed by joining together said two half parts, said elongate throughbore being formed by juxtaposition of said longitudinally-extending grooves;
   a cartridge housing formed by joining together said two half parts, said cartridge housing being formed by juxtaposition of said halves of said cartridge housing; and
   said elongate throughbore being discontinuous at said cartridge housing;
   said elongate throughbore having a trailing part on a trailing side of said cartridge housing and a leading part on a leading side of said cartridge housing.

2. The applicator of claim 1, further comprising:
   a transition tube having a trailing end captured by said leading part of said elongate throughbore;
   said transition tube having a leading end that extends from said elongate throughbore in leading relation thereto; and
   said transition tube leading end adapted to be positioned within a lumen of an elongate needle that has a sharp distal end for penetrating tissue.

3. The applicator of claim 2, wherein said transition tube is formed of polyimide.

4. The applicator of claim 1, further comprising:
   an applicator shell formed by two half shells;
   each of said two half shells having a longitudinally-extending half-channel formed therein;
   an elongate channel formed by joining together said two half shells, said elongate channel being formed by juxtaposition of said two half channels;
   a cartridge housing-receiving recess formed in each of said half shells, each of said half channels being discontinuous at said cartridge housing-receiving recess;
   whereby said disposable inner part, including said cartridge housing, is disposed in sandwiched relation between said half shells when said half shells are in juxtaposition with one another.

5. The applicator of claim 4, further comprising:
   a longitudinally-extending groove formed in an external side wall of each of said half shells;
   a slide member having a generally "U"-shaped configuration including a pair of upstanding side walls projecting from a base wall in parallel relation to one another;
   a longitudinally-extending tongue formed in each side wall of said pair of side walls;
   said longitudinally-extending tongues protruding toward one another so that said longitudinally-extending tongues respectively slideably engage the longitudinally-extending grooves formed in said exterior side walls of said applicator half shells;

whereby said applicator half shells are held in juxtaposition to one another by said slide member to form said applicator shell; and whereby removal of said slide member from said applicator half shells enables cleaning of said slide member and said applicator half shells.

6. The applicator of claim 5, further comprising:

an elongate rod secured to and projecting from said slide member in leading relation thereto; and a "U"-shaped support member secured to a leading end of said elongate rod.

7. The applicator of claim 5, further comprising:

a transversely disposed handle secured to a trailing end of a preselected applicator half shell;

said transversely disposed handle being centered with respect to said applicator shell when said applicator half shells are joined together.

8. A seed cartridge for holding radioactive seeds, comprising:

a seed housing adapted to hold a plurality of radioactive seeds;

said seed housing including a front shielded plate;

a shielded door formed in said front plate;

said shielded door adapted to be opened and closed so that seeds within said seed housing may be viewed when said shielded door is open and so that said seeds within said seed housing may not be viewed when said shielded door is closed, said shielded door protecting an ambient environment from radiation when closed.

9. The cartridge of claim 8, further comprising:

a vertically extending opening formed in said front plate;

a vertically extending tongue formed in opposite vertically extending edges of said vertically extending opening;

a vertically extending groove formed in each vertically extending edge of said shielded door; and a door handle secured to said shielded door so that a user may slide said door in said opening in a first direction to view seeds disposed in said housing and so that a user may slide said door in said opening in a second direction to close said door.

10. An applicator and cartridge combination for depositing radioactive seeds into an internal organ for therapeutic purposes, comprising:

a disposable internal part that comes into contact with a patient's blood and other body fluids;

said disposable inner part made of two elongate half parts;

each of said half parts having a longitudinally-extending groove formed therein;

each of said half parts having half of a cartridge housing formed therein;

an elongate throughbore formed by joining together said two half parts, said elongate throughbore being formed by juxtaposition of said longitudinally-extending grooves;

a cartridge housing formed by joining together said two half parts, said cartridge housing being formed by juxtaposition of said halves of said cartridge housing;

said elongate throughbore being discontinuous at said cartridge housing;

said elongate throughbore having a trailing part on a trailing side of said cartridge housing and a leading part on a leading side of said cartridge housing; and said cartridge housing receiving a seed cartridge that includes a seed housing adapted to house a plurality of radioactive seeds.

11. The applicator and cartridge housing of claim 10, wherein said seed housing has a shielded door formed therein that enables a user to view seeds within said seed housing when said shielded door is open and that protects an ambient environment from radiation when said shielded door is closed.

12. The applicator and cartridge combination of claim 11, further comprising:

a transition tube having a trailing end captured by said leading part of said elongate throughbore;

said transition tube having a leading end that extends from said elongate throughbore in leading relation thereto; and said transition tube leading end adapted to be positioned within a lumen of an elongate needle that has a sharp distal end for penetrating tissue.

13. The applicator and cartridge combination of claim 12, wherein said transition tube is formed of polyimide.

14. The applicator and cartridge combination of claim 10, further comprising:

an applicator shell formed by two half shells;

each of said two half shells having a longitudinally-extending half-channel formed therein;

an elongate channel formed by joining together said two half shells, said elongate channel being formed by juxtaposition of said two half channels;

a cartridge housing-receiving recess formed in each of said half shells, each of said half channels being discontinuous at said cartridge housing-receiving recess;

whereby said disposable inner part, including said cartridge housing, is disposed in sandwiched relation between said half shells when said half shells are in juxtaposition with one another.

15. The applicator and cartridge combination of claim 14, further comprising:

a longitudinally-extending groove formed in an external side wall of each of said half shells;

a slide member having a generally "U"-shaped configuration including a pair of upstanding side walls projecting from a base wall in parallel relation to one another;

a longitudinally-extending tongue formed in each side wall of said pair of side walls;

said longitudinally-extending tongues protruding toward one another so that said longitudinally-extending tongues respectively slideably engage the longitudinally-extending grooves formed in said exterior side-walls of said applicator half shells;

whereby said applicator half shells are held in juxtaposition to one another by said slide member to form said applicator shell; and whereby removal of said slide member from said applicator half shells enables cleaning of said slide member and said applicator half shells.

16. The applicator and cartridge combination of claim 15, further comprising:

an elongate rod secured to and projecting from said slide member in leading relation thereto; and a "U"-shaped support member secured to a leading end of said elongate rod.

17. The applicator and cartridge combination of claim 15, further comprising:

a transversely disposed handle secured to a trailing end of a preselected applicator half shell;

said transversely disposed handle being centered with respect to said applicator shell when said applicator half shells are joined together.

18. An applicator for depositing radioactive seeds into an internal organ for therapeutic purposes, comprising:

a disposable internal part that comes into contact with a patient's blood and other body fluids;

said disposable internal part including a transition tube;

said disposable internal part being disposed in sandwiched relation between two half shells;

a cartridge housing formed in said disposable inner part;

an elongate throughbore formed in said disposable inner part;

said elongate throughbore being discontinuous at said cartridge housing;

said elongate throughbore having a trailing part on a trailing side of said cartridge housing and a leading part on a leading side of said cartridge housing;

a transition tube having a trailing end captured by said leading part of said elongate throughbore so that a lumen of said transition tube is in fluid communication with said elongate throughbore;

said transition tube having a leading end that extends from said elongate throughbore in leading relation thereto;

said transition tube leading end adapted to be positioned within a lumen of an elongate needle that has a sharp distal end for penetrating tissue;

an applicator shell formed by juxtaposition of two half shells;

each of said two half shells having a longitudinally-extending half-channel formed therein;

an elongate channel formed by joining together said two half shells, said elongate channel being formed by juxtaposition of said two half channels;

a cartridge housing-receiving recess formed in each of said half shells, each of said half channels being discontinuous at said cartridge housing-receiving recess;

whereby said disposable inner part, including said cartridge housing, is disposed in said elongate channel in sandwiched relation between said half shells when said half shells are in juxtaposition with one another.

19. The applicator of claim 18, wherein said transition tube is formed of polyimide.

20. An applicator for depositing radioactive seeds into an internal organ for therapeutic purposes, comprising:

an applicator shell formed by two half shells;

each of said two half shells having a longitudinally-extending groove formed therein;

a cartridge housing-receiving recess formed in each of said half shells, each of said half channels being discontinuous at said cartridge housing-receiving recess;

an elongate throughbore formed by joining together said two half shells, said elongate throughbore being formed by juxtaposition of said two longitudinally-extending grooves and being discontinuous at said cartridge-receiving recess;

each of said two half shells having half of a transition tube formed therein at their respective leading ends; and a transition tube formed at the leading end of said applicator shell when said two half shells are placed into juxtaposition with one another.

21. The applicator shell of claim 20, further comprising:

a luer lock base mounted on said transition tube;

said luer lock base being mounted to said transition tube after said half shells are placed into juxtaposition with one another.

\* \* \* \* \*